(12) United States Patent
Marchetti et al.

(10) Patent No.: US 9,976,151 B2
(45) Date of Patent: May 22, 2018

(54) ARTIFICIAL DNA SEQUENCE WITH OPTIMIZED LEADER FUNCTION IN 5'(5'-UTR) FOR THE OVER-EXPRESSION OF RECOMBINANT PROTEINS IN PLANTS AND METHOD FOR THE PRODUCTION OF RECOMBINANT PROTEINS IN PLANTS

(71) Applicant: TRANSACTIVA SRL, Udine (IT)

(72) Inventors: Stefano Marchetti, Pagnacco (IT); Tamara Patti, Buja (IT); Erika Secco, San Donà di Piave (IT)

(73) Assignee: ADIENNE Pharma & Biotech SA, Lugano (CH)

( * ) Notice: Subject to any disclaimer, the term of this patent is extended or adjusted under 35 U.S.C. 154(b) by 0 days. days.

(21) Appl. No.: 14/761,431

(22) PCT Filed: Jan. 15, 2014

(86) PCT No.: PCT/IB2014/058289
§ 371 (c)(1),
(2) Date: Jul. 16, 2015

(87) PCT Pub. No.: WO2014/111858
PCT Pub. Date: Jul. 24, 2014

(65) Prior Publication Data
US 2016/0130593 A1    May 12, 2016

(30) Foreign Application Priority Data
Jan. 16, 2013  (IT) .............................. UD2013A0002

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 2830/30* (2013.01); *C12N 2830/50* (2013.01)

(58) Field of Classification Search
None
See application file for complete search history.

(56) References Cited

FOREIGN PATENT DOCUMENTS

| WO | WO 2008/080954 | * | 7/2008 | ............. C12N 15/82 |
| WO | WO-2008/080954 A1 | | 7/2008 | |

OTHER PUBLICATIONS

Streisinger et al. Frameshift mutations and the genetic code. (1966) Cold Spring Harb. Symp. Quant. Biol.; vol. 31; pp. 77-84.*
Kozak, M. Initiation of translation in prokaryotes and eukaryotes. (1999) Gene; vol. 234; pp. 187-208.*
Liu, D. Design of gene constructs for transgenic maize. (2009) Methods in Molecular Biology: Transgenic Maize; editor: M. P. Scott; Humana Press; vol. 526; pp. 3-20.*
De Amicis et al., Improvement of the pBI121 plant expression vector by leader replacement with a sequence combining a poly(CAA) and a CT motif. *Trans. Res.* 16(6): 731-8 (2007).
Fan et al., Untranslated regions of diverse plant viral RNAs vary greatly in translation enhancement efficiency. *BMC Biotechnol.* 12(1): 22 (2012).
International Search Report and Written Opinion of the International Searching Authority issued in connection with International Application No. PCT/IB2014/058289, dated Apr. 29, 2014.
International Preliminary Report on Patentability, Chapter II, issued in connection with International Application No. PCT/IB2014/058289, dated Feb. 3, 2015.

* cited by examiner

*Primary Examiner* — Cathy Kingdon Worley
(74) *Attorney, Agent, or Firm* — Sterne, Kessler, Goldstein & Fox P.L.L.C.

(57) ABSTRACT

Artificial DNA of a 5'-UTR leader region, which artificial DNA is effective in increasing the expression of recombinant proteins in plants, and comprises, along the 5'→3' direction, an Inr initiator site and a Kozak or Kozak-like consensus sequence, and also comprises, between the Inr initiator site and the Kozak or Kozak-like consensus sequence, a plurality of poly(CAA) and a plurality of poly(CT) regions, in the same number as the poly(CAA) regions wherein at least one, optionally each one, poly (CAA) region, in the 5'→3' direction, is upstream of a poly(CT) region and at least one poly(CAA) region, in the 5'→3' direction, is contiguous with a poly(CT) region, wherein the artificial DNA provides the absence of A/T-rich motifs, the absence of trinucleotide elements ATT, the absence of trinucleotide elements CTG and the absence of homopolymeric tracts, that is, sequences consisting of more than 3, optionally more than 4, identical nucleotides.

14 Claims, 3 Drawing Sheets

SEQUENCE LISTING

<160> NUMBER OF SEQ ID NOS: 5

<210> SEQ ID NO 1
<211> LENGTH: 75
<212> TYPE: DNA
<213> ORGANISM: Artificial
<220> FEATURE:
<223> OTHER INFORMATION: Artificial DNA of 5'-UTR region

<400> SEQUENCE: 1
acacgaagtt tccaacaaca acaacaacaa caactctctc tctcaacaac aacaacaaca    60
acaaagctct ctaga                                                    75

<210> SEQ ID NO 2
<211> LENGTH: 77
<212> TYPE: DNA
<213> ORGANISM: Artificial
<220> FEATURE:
<223> OTHER INFORMATION: Artificial DNA of a 5'-UTR region

<400> SEQUENCE: 2
tcacatcaag tttccaacaa caacaacaac aacaactctc tctctcaaca acaacaacaa    60
caacaaagct ctctaga                                                  77

<210> SEQ ID NO 3
<211> LENGTH: 73
<212> TYPE: DNA
<213> ORGANISM: Artificial
<220> FEATURE:
<223> OTHER INFORMATION: Synthetic polynucleotide

<400> SEQUENCE: 3
acacgtattt ttacaacaat accaacaaca acaacaacaa acaacattac aattacgtat    60
ttctctctct aga                                                      73

<210> SEQ ID NO 4
<211> LENGTH: 77
<212> TYPE: DNA
<213> ORGANISM: Artificial Sequence
<220> FEATURE:
<223> OTHER INFORMATION: TMV omega leader sequence

<400> SEQUENCE: 4
acctcgagta ttttacaac aattaccaac aacaacaaac aacaaacaac attacaatta    60
ctatttacaa ttacacc                                                  77

<210> SEQ ID NO 5
<211> LENGTH: 45
<212> TYPE: DNA
<213> ORGANISM: Artificial
<220> FEATURE:
<223> OTHER INFORMATION: AMV leader sequence

<400> SEQUENCE: 5
acctcgagtt tttatttta attttctttc aaatacttcc atccc                    45

ARTIFICIAL DNA SEQUENCE WITH OPTIMIZED LEADER FUNCTION IN 5'(5'-UTR) FOR THE OVER-EXPRESSION OF RECOMBINANT PROTEINS IN PLANTS AND METHOD FOR THE PRODUCTION OF RECOMBINANT PROTEINS IN PLANTS

INCORPORATION BY REFERENCE OF MATERIALS SUBMITTED ELECTRONICALLY

Incorporated by reference in its entirety is a computer-readable nucleotide/amino acid sequence listing as follows: 1,773 byte ASCII text file named "49828_SubSeqListing.txt"; created Jun. 16, 2016.

FIELD OF THE INVENTION

The present invention concerns an artificial DNA sequence with optimized leader function in 5' (5'-UTR) for the over-expression of recombinant proteins in plants and a method for the production of recombinant proteins in plants.

BACKGROUND OF THE INVENTION

There are many approaches that can be adopted in order to improve the expression of heterologous genes in plants. Indeed, all the elements that make up a gene exert, or can exert, a control function on gene expression, modulating the transcription and/or translation process. The untranslated sequences present at the 5'- and 3' ends of the mRNA (called 5'-UTR and 3'-UTR, where UTR stands for "untranslated region") are no exception to this and indeed must be considered preferential targets for suitable modifications since, to a large extent, they determine the translation efficiency and the turn-over of the mRNA itself. In fact, copious evidence proves that:

- the m7Gppp (5'-cap) structure present at the 5' terminal of the mRNA is essential for recruiting the eIF4F complex able to bond the ribosomal 40S subunit (Franks and Likke-Andersen, 2008);
- through the eIF4G component, the eIF4F complex interacts with the poly(A) tail present at the 3' terminal of the mRNA, allowing the latter to assume a circular structure (Franks and Likke-Andersen, 2008);
- poly(A) tail and eIF4F complex reduce the enzymatic hydrolysis of the 5'-cap structure and hence prevent the rapid degradation of the mRNA by cytoplasmic exo-nucleases active on the mono-phosphate 5' terminals (Franks and Likke-Andersen, 2008);
- the 5'-UTR sequence can contain elements able to influence the formation of the 5'-cap structure, the bond of the latter with the eIF4E factor, the recruiting of the ribosomal 40S subunit, the constitution of polysomes, the spontaneous dissociation rate of the 43S complex, the recognition of the authentic translation start codon AUG;
- the 5'-UTR sequence can also contain sequences that represent bonding sites to the DNA for specific transcription factors, and hence can modify the transcription activity of the promoters upstream.

It is therefore evident that the 5'-UTR, also called leader region, needs to be particularly considered in plant engineering programs in order to increase the expression level of recombinant proteins.

However, for various reasons, it is not at all easy to design high-efficiency leader sequences, even for a person of skill in the art. Firstly, the great variability in the sequence observable between leader regions of different genes belonging to the same genome or to related genomes must be considered. This variability makes it very difficult to identify potential tracts able to confer an improved characteristic on the leader, and practically impossible to predict possible interactions with other elements or sequences that make up the 5'-UTR region. Secondly, the overall length of the leader region must possibly be contained within 100-120 bp, preferably 80 bp, so as not to increase the frequency of spontaneous dissociation of the 43S complex from the region itself. This imposes a strict choice of the components that will actually be used in the construction of the leader tract, to the detriment of others. Thirdly, the leader region should not contain palindrome sequences or a nucleotide composition rich in G/C, so as to prevent the formation of secondary structures in the transcript that cannot be resolved through the intervention of eIF4A. Finally, a minority portion, but in any case significant, of the sequence (about 10%) cannot vary freely but must contain essential functional elements, such as, specifically, the Inr initiator site and the Kozak motif or equivalent Kozak-like motif.

Application WO 2008/080954 describes the combination of repeated CAA elements with repeated CT elements inside 5'-UTR sequences usable to increase the expression of recombinant proteins in plants. Furthermore, it also describes the co-presence of poly(CAA) and poly(CT) with the transcription initiator site (Inr) of the CaMV 35S promoter, that is, the cauliflower mosaic virus (Guilley et al., 1982) and/or with the ACAATTAC octamer from the TMV Ω leader (Gallie and Walbot, 1992). In fact, WO 2008/080954 describes a leader sequence called LLTCK containing for example all the elements cited above:

1. Inr site of CaMV 35S gene for an efficient mRNA capping;
2. Poly(CAA) region similar to the "translational enhancer" present in the TMV Ω leader (Gallie and Walbot, 1992);
3. Sequence rich in CT elements, similar to some plant leaders (Bolle et al., 1996);
4. Octamer of TMV Ω leader.

The effect of the LLTCK leader in WO 2008/080954 was assessed in tobacco, using the leader of the CaMV 35S gene for comparison, which is present in a large number of commercial vectors, by determining the expression levels of the uidA reporter gene (coding for enzyme β-glucuronidase, GUS) under the control of the constitutive CaMV 35S promoter. The LLTCK leader determined an increase in concentration of the GUS enzyme equal to 8-12 times that of the control leader.

There is however a need to further increase the efficiency of the 5'-UTR tract for the expression of transgenes, and hence of recombinant proteins in plants.

In particular, in order to further increase the efficiency of the 5'-UTR tract for the expression of transgenes in plants compared with the state of the art, considering that LLTCK is the only synthetic high-efficiency leader whose effects on the transcription and translation processes of genetic information are known, it may be useful to consider this leader as a model or starting point for interventions to improve them.

As we said, WO 2008/080954 provides to combine repeated CAA elements with repeated CT elements and identifies a series of factors able to make the advantage of said combination more evident.

A preferential application is associated with each factor. Particular importance is given to the presence of the octamer motif ACAATTAC harbored by the TMV Ω leader; in fact, according to WO 2008/080954, an efficient leader can derive from joining tracts of the TMV Ω leader with a region bearing repeated CT motifs.

Inside the Ω leader known from WO 2008/080954, repeated sequences of different types can be seen: one such sequence is represented by the trinucleotide CAA repeated 11 times, although not always contiguously; the other sequence is represented by the octamer motif ACAATTAC repeated 3 times.

It has been experimentally demonstrated that both sequences can cause a great increase in gene expression, acting on a post-transcriptional level.

Although the octamer contains a trinucleotide CAA, the enhancement of gene expression is connected to the presence of the entire sequence, and not of the CAA alone.

It is important to underline that the octamer contains an A/T-rich tract, that is, AATTA, which in turn includes the ATT triplet.

As a possible preferential technical solution, the inventors of WO 2008/080954 indicate keeping the octamer sequence ACAATTAC, even if this contains the AATTA sequence, and therefore a non-canonical translation start site ATT.

Obviously, they believe that the inclusion of the octamer motif mentioned above is more important, even if this entails the introduction of an A/T-rich sequence and with it a putative translation start codon. It must be underlined that in the ID sequence no 1 (LLTCK) of WO 2008/080954, other A/T-rich sequences are specifically noted, positioned respectively:

1. immediately downstream of the initiator site (TATTTTTA);
2. inside the poly(CAA) (AATA) tract;
3. at the end of this tract, in a site again involving the octamer (ATTA);
4. just downstream of the octamer (TATTT).

Three sequences out of four carry the triplet ATT, like the octamer.

We shall now give, for comparison, the known sequence LLTCK leader, highlighting the A/T-rich regions (underlined) and the ATT triplets (bigger character); the tract ACAATTAC in bold corresponds to the octamer motif:

ACACGTATTTTTACAACAATACCAACAACAACAACAACAAACAA

CATTACAATTACGTATTTCTCTCTCTAGA

We also underline that this known LLTCK sequence does not provide any poly(CAA) region contiguous with a poly (CT) region.

In this case too, although they are aware of the presence of non-canonical translation start sites inside the A/T-rich regions, the inventors of WO 2008/080954 have provided to use said regions in the construction of an efficient leader like LLTCK.

In fact, the A/T-rich sequences, specifically type 1 and 4 as described above, are found not only in the TMV Ω leader but also at the core of the AMV leader commonly used as a translation enhancer as an alternative to Ω.

Hereafter, for comparison, we give the sequences of the TMV Ω leader (a) and AMV leader (b), highlighted, the A/T-rich regions (underlined) and the ATT triplets (bigger character):

(a)                                                                                     (SEQ ID NO: 4)
ACCTCGACTATTTTTACAAC
AATTACCAACAACAACAAACAACAAACAA
CATTA(AATTAC)ATTACAATTACACC (b)                                                                                     (SEQ ID NO: 5)
ACCTCGACTTTTTATTTTTAATTTTCTTTCAAATACTTCCATCCC.

With regard to the actual significance of the ATT triplets in inducing the start of the translation process in an unwanted point of the mRNA inside the leader, it must be noted here that the authentic translation start codon (ATG) needs a context sequence adequate to be recognized as such by the translation complex; it is very likely for a person of skill in the art that an adequate context must equally exist for the recognition of non-canonical translation start triplets such as ATT and CTG.

However, the recognition contexts of the triplets are not known at the moment, and therefore the person of skill is not able to establish, by assessing the state of the art, if and how much a certain triplet ATT (or CTG) really represents a non-canonical translation start site.

Faced by this evidence, in determining the choice of using Ω, AMV or leaders deriving therefrom, it is the positive effect, experimentally proven, of the inclusion of the Ω leader or AMV leader on the level of gene expression that is important.

The person of skill knows, however, that if an ATT or CGT triplet inside the leader were actually interpreted as a translation start codon, a different protein would be produced, not the programmed one, and this could cause problems of functional and structural bio-equivalence, particularly critical in the case of proteins for which a therapeutic application is intended.

The inventors of WO 2008/080954, working mainly in the pharmaceutical field, are aware of the potential risks and, prudently, construct their 5'-UTR sequence by putting all the ATT triplets at a reciprocal distance which is always a multiple of 3, and a stop codon (TAG) in frame with respect to them, toward the end of the leader sequence. Even more ingeniously, the end of the LLTCK sequence is represented by the restriction site for Xba I (TCTAGA) which has the triple function of bearing the stop codon (TAG), of contributing to the formation of a poly(CT) region, of making a possible context favorable to the recognition of an authentic start codon located immediately downstream, as well as of constituting an extremely useful cloning site in 5' of the desired coding sequence.

Other persons of skill behave differently and simply leave the ATT triplets inside the relative A/T-rich sequences.

In fact, it is common to find synthetic leaders with a programmed sequence bearing ATT triplets even in a divergent position from the authentic reading frame.

From the above it may be concluded that, like other patents and publications preceding this description, WO 2008/080954:
1. does not teach to remove A/T-rich motifs from 5'-UTR sequences, but rather the exact opposite;
2. does not teach to remove ATT triplets from omega-derived or AMV-derived 5'-UTR sequences, but rather the exact opposite;
3. does not teach how to make contexts favorable to gene expression in the absence of A/T-rich motifs, whether or not they bear ATT triplets;

4. does not teach how to construct more efficient variants to the LLTCK leader used in the examples of WO 2008/080954.

All this considered, the need to remove A/T-rich sequences and ATT triplets is in no way suggested or promoted, either explicitly or implicitly by the state of the art, and therefore it is anything but obvious for a person of skill in the art.

Furthermore, since every nucleotide replacement, deletion or addition is potentially able to generate leaders with an unexpected behavior, also the effect of such a removal, like any other manipulations of the 5'-UTR sequence, is anything but obvious for a person of skill in the art.

Therefore, the present invention proposes, in a new and inventive manner, the synthesis of 5'-UTR variants endowed with new elements or new combinations of elements, which constitute an advantageous technical solution, able to modify and significantly improve the state of the art. The Applicant has devised, tested and embodied the present invention to obtain these and other purposes and advantages.

Unless otherwise defined, all the technical and scientific terms used here and hereafter have the same meaning as commonly understood by a person with ordinary experience in the field of the art to which the present invention belongs. Even if methods and materials similar or equivalent to those described here can be used in practice and in the trials of the present invention, the methods and materials are described hereafter as an example. In the event of conflict, the present application shall prevail, including its definitions. The materials, methods and examples have a purely illustrative purpose and shall not be understood restrictively.

SUMMARY OF THE INVENTION

The present invention is set forth and characterized in the independent claims, while the dependent claims describe other characteristics of the invention or variants to the main inventive idea.

In accordance with the above purpose, the present description concerns the field of plant biotechnology and in particular deals with the raising of the productive level of recombinant proteins in genetically modified plants by using artificial leaders suitably constructed according to the present description, obtained through artificial synthesis and the product of the intellect, since they are not found in nature.

Some forms of embodiment described here refer to an artificial DNA of a 5'-UTR leader region for the expression of transgenes in plants. The artificial DNA according to features of the present description is effective in increasing the expression of transgenes in plants and comprises, along the 5'→3' direction, an Inr initiator site and a Kozak or Kozak-like consensus sequence respectively at the corresponding 5'- and 3' terminals. The artificial DNA according to features of the present description also comprises, between the Inr initiator site and the Kozak or Kozak-like consensus sequence, a plurality of poly(CAA) or (CAA)$_n$ regions, each formed by an oligonucleotide that consists of two or more copies of a CAA element contiguous with each other, and a plurality of poly(CT) or (CT)$_m$ regions in the same number as the poly(CAA) regions and each formed by an oligonucleotide that consists of two or more copies of a CT element contiguous with each other, wherein at least one, optionally each one, poly(CAA) region, in the 5'→+3' direction, is upstream of a poly(CT) region, that is, in position 5', and at least one poly(CAA) region, in the 5'→3' direction, is contiguous with a poly(CT) region.

In some forms of embodiment, the artificial DNA provides the presence of sequences that cannot be associated with A/T-rich motifs, that is, it provides an absence of A/T-rich motifs.

In some forms of embodiment, A/T-rich motifs not present in the artificial DNA according to the present description can be defined as tracts or sequences consisting of more than 3, optionally more than 4, nucleotides adenine (A) and/or thymine (T), in any combination with each other.

In some forms of embodiment, the artificial DNA provides the presence of sequences that cannot be associated with trinucleotide elements ATT, that is, it provides an absence of trinucleotide elements ATT.

In some forms of embodiment, the artificial DNA provides the presence of sequences that cannot be associated with trinucleotide elements CTG, that is, it provides an absence of trinucleotide elements CTG.

In some forms of embodiment, the artificial DNA provides an absence of homopolymeric tracts, that is, sequences consisting of more than 3, optionally more than 4, identical nucleotides.

In some forms of embodiment, the value n can be chosen the same for the poly(CAA) regions or can be chosen autonomously for the various poly(CAA) regions, that is, a different value n can be selected for at least one of the poly(CAA) regions with respect to one or more other poly(CAA) regions.

In some forms of embodiment, n is an integer greater than or equal to 2, optionally comprised between 3 and 9, optionally between 4 and 8, optionally between 5 and 7.

In some forms of embodiment, for at least one poly(CAA) region n is equal to 7, for example for at least two poly(CAA) regions n is equal to 7.

In some forms of embodiment, the value of m can be chosen the same for the poly(CT) regions or it can be chosen autonomously for the various poly(CT) regions, that is, a different value of m can be selected for at least one of the poly(CT) regions with respect to the value of m of one or more other poly(CT) regions.

In some forms of embodiment, m can be an integer greater than or equal to 2, optionally comprised between 3 and 5. According to some aspects, for at least one poly(CT) region, m is equal to 5. According to other aspects, for at least one poly(CT) region, m is equal to 3. In possible implementations, for one poly(CT) region, m is equal to 5 and for another poly(CT) region, m is equal to 3.

In some forms of embodiment, the artificial DNA contains two poly(CAA) regions and two poly(CT) regions, of which one poly(CAA) region can be contiguous to one poly(CT) region and possibly another poly(CAA) region may not be contiguous with another poly(CT) region.

In some forms of embodiment, a first poly(CAA) region is upstream, that is, in position 5', of a first poly(CT) region and a second poly(CAA) region is downstream of said first poly(CT) region and upstream, that is, in position 5', of a second poly(CT) region.

In some forms of embodiment, the first poly(CAA) region is contiguous with the first poly(CT) region.

In other forms of embodiment, the first poly(CAA) region is not contiguous with the first poly(CT) region.

In some forms of embodiment, the second poly(CAA) region is contiguous with the first poly(CT) region.

In other forms of embodiment, the second poly(CAA) region is not contiguous with the first poly(CT) region.

In some forms of embodiment, the second poly(CAA) region is contiguous with the second poly(CT) region.

In other forms of embodiment, the second poly(CAA) region is not contiguous with the second poly(CT) region.

In some forms of embodiment, for the first poly(CAA) region the value of n is equal to 7, that is, it comprises 7 copies of the CAA triplet.

In some forms of embodiment, for the second poly(CAA) region the value of n is equal to 7, that is, it comprises 7 copies of the CAA triplet.

In some forms of embodiment, for the first poly(CT) region the value of m is equal to 5, that is, it comprises 5 copies of the CT dinucleotide.

In some forms of embodiment, for the second poly(CT) region the value of m is equal to 3, that is, it comprises 3 copies of the CT dinucleotide.

In some forms of embodiment, between the second poly (CAA) region and the second poly(CT) region there is an AG sequence. In some forms of embodiment, between the second poly(CAA) region and the second poly(CT) region there is exclusively the AG sequence.

In some forms of embodiment, the Inr initiator site is the CaMV 35S transcription start site or it is an Inr initiator site with a consensus sequence 5'-YYANWYY-3', where:
Y=C, T;
N=A, C, G, T;
W=A, T.

In possible example forms of embodiment, the Inr initiator site is 5'-TCACATC-3'.

In some forms of embodiment, between the Inr initiator site and the first poly(CAA) region along the 5'→3' direction there is an AAGTTTC sequence. In some forms of embodiment, between the Inr initiator site and the first poly(CAA) region along the 5'→3' direction there is exclusively the AAGTTTC sequence.

In some forms of embodiment, the artificial DNA has a length comprised between 40 and 150 bp.

In some forms of embodiment, the artificial DNA has a GC content of less than 50%.

In some forms of embodiment, the artificial DNA comprises the sequence shown in SEQ ID NO: 1, or the sequence shown in SEQ ID NO: 2, both included in the attached sequence listing.

In some forms of embodiment, the Kozak or Kozak-like consensus sequence is a sequence that requires the presence of an element R which is a purine in position −3, that is, located in the third position upstream of the translation start codon.

In some forms of embodiment, the artificial DNA according to the present invention does not contain the octamer ACAATTAC.

Some forms of embodiment described here concern an expression vector comprising artificial DNA of a 5'-UTR leader region effective in increasing the expression of recombinant proteins in plants, in particular for example human proteins, according to forms of embodiment described here.

In some forms of embodiment, the expression vector comprises:

i) an endosperm-specific promoter of natural or artificial origin upstream, that is, in position 5', of a nucleotide sequence of natural or artificial origin encoding the mature form of a protein;

ii) the artificial DNA of the 5'-UTR leader region effective in increasing the expression of recombinant proteins in plants as described here;

iii) a nucleotide sequence of natural or artificial origin encoding a signal peptide to target the recombinant protein inside the lumen of the endoplasmic reticulum of the cells that make up the tissue of the endosperm and thus to favor its tissue accumulation;

iv) the nucleotide sequence of natural or artificial origin encoding the mature form of the protein of interest;

v) a 3'-UTR region of natural or artificial origin.

In some forms of embodiment, the promoter i) is the promoter of the gene for glutelin 4 of rice (GluB4).

In some forms of embodiment, the nucleotide sequence of element iii) is the sequence PSGluB4 encoding the signal peptide used in rice to convey the precursor of glutelin 4 inside the endoplasmic reticulum.

In some forms of embodiment, the nucleotide sequence of element iv) is the sequence encoding the mature human form of the enzyme acid beta-glucosidase.

In some forms of embodiment, the 3'-UTR region of element v) is the NOS terminator or the terminator of the gene GluB4.

Some forms of embodiment described here concern a bacterial strain bearing a plasmid containing an artificial DNA sequence as described here, in particular for example chosen from a group comprising the species *Escherichia coli*, *Agrobacterium tumefaciens* and *Agrobacterium rhizogenes*.

Some forms of embodiment described here concern an engineered bacterial strain containing an artificial DNA sequence according to forms of embodiment as described here, irrespective of the type of host organism.

Some forms of embodiment described here concern transformed plant cells with expression vectors containing the artificial DNA sequence as described here, under the control of a promoter chosen from a group comprising a constitutive promoter, a tissue-specific promoter and in particular for example seed-specific, an inducible promoter, a promoter with phase-dependent transcriptional activity, a promoter active in chloroplast and a promoter active in mitochondria.

Some forms of embodiment described here concern plants characterized by the transitory expression of any protein whatsoever whose messenger RNA contains the artificial DNA sequence described here; by transitory expression we mean the production of said protein by viral vectors, agroinfiltration, bombardment with microparticles, electroporation.

Some forms of embodiment described here concern dicot plants stably transformed with expression vectors containing the artificial DNA sequence according to forms of embodiment as described here.

In some forms of embodiment, the dicot plants comprise one or more species belonging to the Solanaceae, Papilonaceae and/or Cruciferae families.

Some forms of embodiment described here concern the progeny of the dicot plants as above.

Some forms of embodiment described here concern transformed monocot plants with expression vectors containing the artificial DNA sequence according to forms of embodiment described here.

In some forms of embodiment, the monocot plants comprise one or more species belonging to the Graminaceae (Poaceae) family, such as for example cultivated rice (*Oryza sativa* L.), maize (*Zea mays* L.), barley (*Hordeum vulgare* L.) and/or wheat (*Triticum* spp.).

Some forms of embodiment described here concern the progeny of the monocot plants as above.

Some forms of embodiment concern the artificial DNA sequence according to forms of embodiment described here for a use chosen from a group comprising:
  use for biotechnological production of molecules;
  use for the synthesis of recombinant proteins, in particular for example intended to induce resistance to viral, bacterial or fungal pathogens, or intended to induce resistance to herbicides or for obtaining an altered composition in fatty acids in the raw material and in the products deriving therefrom, or for obtaining an altered nutritional value of the raw material and the products deriving therefrom, or for the production of fuels, rubbers and/or bioplastics;
  use for the synthesis of industrial enzymes and commercial proteins;
  use for the synthesis of pharmaceutical proteins;
  use for the synthesis of vaccines chosen from a group comprising: orally administered vaccines intended for humans or animals, injectable vaccines intended for humans or animals, patient-specific injectable vaccines, preferably idiotype-specific, to be used in treating tumors of the lymphatic system;
  use for the synthesis of proteins involved in the production of secondary metabolites;
  use for the synthesis of proteins usable directly or indirectly as factors in the identification and/or selection of transformed cells.

Some forms of embodiment described here concern the seed of a plant transformed for the expression of a human protein, in particular for example a human lysosomal enzyme, containing an expression vector according to forms of embodiment described here.

Some forms of embodiment described here concern a seed as above, for use in therapeutic treatment, in particular for example for use in enzyme replacement therapy, even more in particular for example in the following diseases: Gaucher's disease, glycogenosis type II or Pompe's disease, Fabry's disease, Niemann-Pick disease type B, Mucopolysaccharidosis I, II, IV.

Some forms of embodiment concern a method for the production of recombinant proteins in plants, comprising the transformation of the plants using an expression vector as described here.

In some forms of embodiment, the transformation of the plants is effective in achieving the confinement of the protein in an endosperm not absorbed by the embryo and to allow that the presence of high quantities of the protein in the endosperm of the seed does not cause negative effects on seed viability and germination speed.

In some forms of embodiment, the method provides to accumulate the protein inside the endosperm of the plant seed, in particular for example the protein is accumulated in the endosperm inside the protein storage vacuoles (PSV) or protein bodies (PB).

In some forms of embodiment, the expression vector is introduced in bacterial strains which are used, directly or indirectly, for plant transformation, where the bacterial strain can be chosen from a group comprising the species *Escherichia coli*, *Agrobacterium tumefaciens* and *Agrobacterium rhizogenes*.

In some forms of embodiment, the plants transformed are cereals.

In some forms of embodiment, the bacterial strain is used for the transformation of embryogenic rice calli (*Oryza sativa* ssp. *japonica*).

In some forms of embodiment, the recombinant protein is a lysosomal enzyme, in particular for example human acid beta-glucosidase, or for example human acid alpha-glucosidase.

In some forms of embodiment, the method comprises the industrial processing of the plant seed.

In some forms of embodiment, the industrial processing of the plant seed provides to husk and polish the mature seeds collected from transformed cereal plants in order to remove the fibrous component, the germ, and the aleuronic layer containing protein contaminants.

In some forms of embodiment, the method comprises purification of the protein obtained.

In some forms of embodiment, the purification provides, in order, a chromatography with hydrophobic interactions, a chromatography with ion exchange and a gel-filtration.

In some forms of embodiment, the purification provides to apply chromatographic resins similar in chemical composition and/or structure and/or function, to partly modify the elution parameters, and to duplicate a passage for recharging the eluted fraction in the column.

BRIEF DESCRIPTION OF THE DRAWINGS

These and other characteristics of the present invention will become apparent from the following description of some forms of embodiment, given as a non-restrictive example with reference to the attached drawings wherein.

DETAILED DESCRIPTION OF SOME FORMS OF EMBODIMENT

Figure 1:
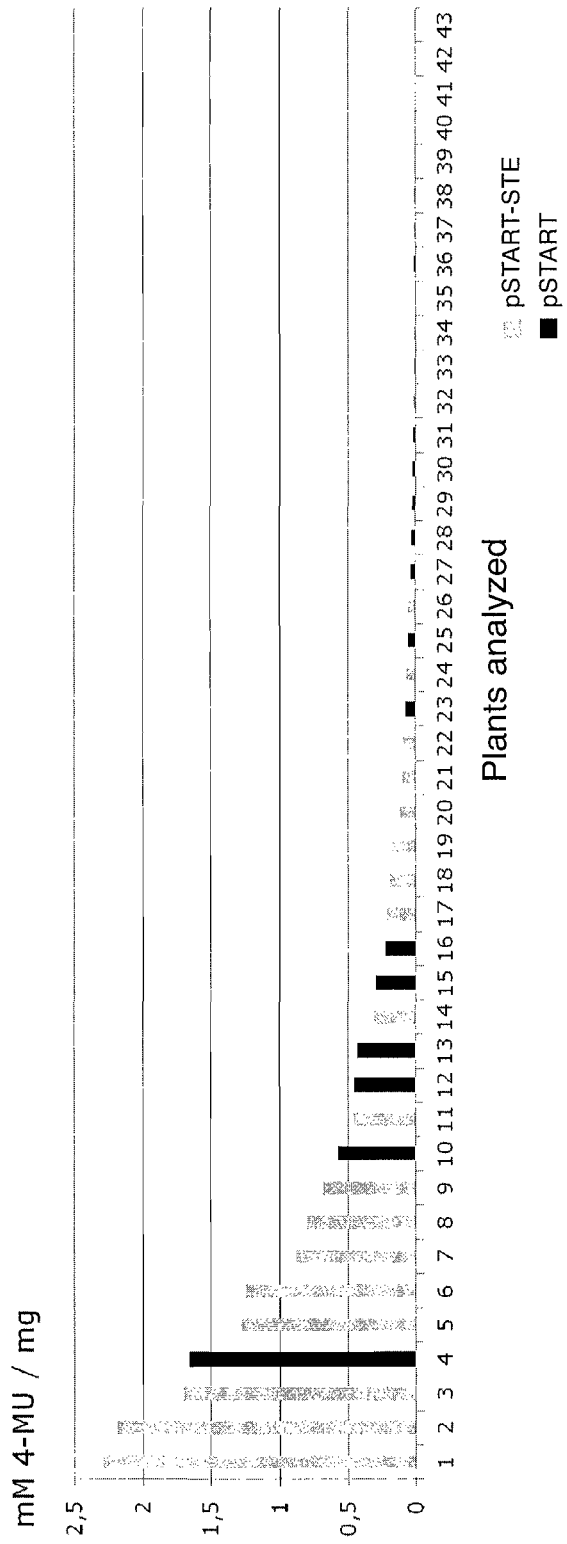
FIG. 1 shows the distribution of the values obtained using a 4-MUG assay in tobacco plants transformed with pSTART and pSTART-STE.

We shall now refer in detail to the various forms of embodiment of the present invention, of which one or more examples are described hereafter. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

In the attempt to further increase the efficiency of the 5'-UTR tract for the expression of transgenes in plants compared with the state of the art, a sequence of artificial DNA has been devised, hereafter called STE, STE sequence or STE leader, containing repeated CAA trinucleotide elements and repeated CT dinucleotide elements, as disclosed by WO 2008/080954, which STE sequence is optimized for the over-expression of recombinant proteins in plants.

It should be noted that this new and inventive STE sequence has given an increase in gene expression in two unrelated plant species and in association with different promoters, terminators and coding sequences.

Starting from the state of the art as discussed above, Applicant carried out other experiments intended to develop a new type of leader according to the present description.

In particular, Applicant considered that many viruses that attack plants produce messengers without 5'-cap and in many cases also without the poly(A) tail. This evidence let the Applicant suppose that in these viruses the untranslated regions in 5' (5'-UTR) and 3' (3'-UTR) harbor sequences able to functionally replace the 5'-cap structure and the poly(A) tail respectively. These sequences, indispensable in the viral messenger, could however be less important inside leaders of eukaryotic genes, and specifically plant genes, because the messengers they produce always have the 5'-cap and, except for rare exceptions, also the poly(A) tail.

In particular, Applicant hypothesized that the sequences essential to viral leaders but not to leaders of eukaryotic genes correspond to one or more A/T-rich sequences, such as for example those previously indicated by numbers 1-4 inside LLTCK or portions thereof. Therefore, a design activity was started with the intention of obtaining a synthetic leader sequence totally devoid of A/T-rich sequences and hence without Ω octamer regions and ATT triplets; in the formation of the new leader, it was also decided to exclude trinucleotide CTG and homopolymer tracts formed by the repetition of any nucleotide whatsoever. To keep the length of the leader substantially unchanged with respect to WO 2008/080954, the A/T-rich regions were replaced by repeated CAA and CT motifs. The resulting sequence, called STE, was compared with the seq. ID no. 1 of WO 2008/080954, in different contexts.

The results obtained allowed to establish that, in accordance with Applicant's hypothesis but unlike what was expected based on the state of the art available to the person of skill, eliminating A/T-rich elements and replacing them with repeated CAA and CT elements always causes a significant increase in the expression of the reporter genes used in the comparative experiments between leaders, even if said A/T-rich elements are preserved inside viral leaders commonly used as translation enhancers. Compared with LLTCK in WO 2008/080954, the new type of 5'-UTR according to the present description represents a better technical solution useful for solving, in the industrial field, the problems connected to efficient production, extraction and purification of heterologous proteins.

Therefore, forms of embodiment described here provide artificial DNA of a 5'-UTR leader region effective in increasing the expression of recombinant proteins in plants, comprising along the 5'→3' direction a plurality of poly(CAA) or $(CAA)_n$ regions, and a plurality of poly(CT) or $(CT)_m$ regions in the same number as the poly(CAA) regions.

In some forms of embodiment, each poly(CAA) region is formed by an oligonucleotide that consists of two or more copies of a CAA element contiguous with each other.

In some forms of embodiment, each poly(CT) region is formed by an oligonucleotide that consists of two or more copies of a CT element contiguous with each other.

In some forms of embodiment, at least one, optionally each one, poly(CAA) region, in the 5'→3' direction, is upstream of a poly(CT) region, that is, in position 5'.

In some forms of embodiment, at least one poly(CAA) region, in the 5'→3' direction, is contiguous with a poly(CT) region.

In some forms of embodiment, n is an integer, which can be selected equal or different among the poly(CAA) regions, greater than or equal to 2, optionally comprised between 3 and 9, optionally between 4 and 8, optionally between 5 and 7. For example, the value n can be the same for the poly(CAA) regions and can be, for example, equal to 7.

In some forms of embodiment, m is an integer, which can be selected equal or different among the poly(CT) regions, greater than or equal to 2, optionally comprised between 3 and 5. For example, the value m can be different for the poly(CT) regions and can be, for example, equal to 3 or 5.

Although in general the values of n and m can be selected different from each other, some forms of embodiment may also be provided in which the values of n and m are selected the same as each other.

In possible implementations, two poly(CAA) regions and two poly(CT) regions may be provided. Along the 5'→3' direction a first poly(CAA) region may be provided, a subsequent first poly(CT) region, contiguous to the preceding first poly(CAA) region, a successive second poly(CAA) region, contiguous to the preceding first poly(CT) region and a successive second poly(CT) region, not contiguous to the second poly(CAA) region.

In some forms of embodiment, the STE sequence can be characterized by aspects that are an improvement compared with WO 2008/080954, and referred to one or more of the following features, intended to render the STE sequence more compatible with, an eukaryotic expression system:

1. Absence of A/T-rich motifs, that is, sequences consisting of more than 3, optionally more than 4, nucleotides adenine (A) and/or thymine (T), in any combination thereof;
2. Absence of trinucleotide elements ATT;
3. Absence of trinucleotide elements CTG;
4. Absence of homopolymeric tracts, that is, sequences consisting of more than 3, optionally more than 4, identical nucleotides.

In other words, the artificial DNA according to the present description does not contain any of the following components: A/T-rich elements, trinucleotide elements ATT, trinucleotide elements CTG and homopolymeric tracts, that is, sequences consisting of more than 3, optionally more than 4, identical nucleotides.

In some forms of embodiment, an artificial DNA sequence described here can contain an Inr site. The Inr site can have a 5'-YYANWYY-3' sequence, with the limitations as above in points 1 (absence of A/T-rich motifs) and 2

(absence of trinucleotide elements ATT), where Y=C, T; N=A, C, G, T; W=A, T; alternatively, the Inr site can have a 5'-ACACG-3' sequence (transcription start site for 35S of CaMV).

In some forms of embodiment, at the 3' end, the leader region can also contain a nucleotide context favorable to the recognition of the authentic ATG translation start codon (Kozak or Kozak-like motif or consensus sequence). A Kozak or Kozak-like motif or consensus sequence requires the presence of an R element which is a purine (adenine "A" or guanine "G") in position 3 upstream of the translation start codon, to identify the appropriate context for recognizing the authentic translation start codon. By position 3 upstream of the start codon (or position −3) we mean a position 3 nucleotides upstream of element "A" of the ATG codon to which position+1 is conventionally assigned. The Kozak or Kozak-like sequence can be successive and contiguous for example to the second poly(CT) region as discussed above.

Furthermore, in some forms of embodiment the STE leader sequence described here can have a length comprised between 40 and 150 bp and can optionally have a GC content of less than 50%.

One example of a leader sequence, called SEQ ID NO: 1, according to some forms of embodiment, is:

```
(1)                                    (SEQ ID NO: 1)
5'-ACACGAAGTTTCCAACAACAACAACAACAACAACTCTCTCTCT

CAACAACAACAACAACAACAAAGCTCTCTAGA-3'.
```

Another example of a leader sequence, called SEQ ID NO: 2, according to some forms of embodiment, is:

```
(2)                                    (SEQ ID NO: 2)
5'-CACATCAAGTTTCCAACAACAACAACAACAACAACTCTCTCTCT

CAACAACAACAACAACAACAAAGCTCTCTAGA-3'
```

In some forms of embodiment, the leader sequence described here, such as for example SEQ ID No: 1 and SEQ ID No: 2, can have an Inr initiator site in 5', such as the transcription start site of CaMV 35S (SEQ ID No: 1, variant 1) or an Inr site with a consensus sequence typical of eukaryotic genes, 5'-YYA$^{+1}$NWYY-3', where A$^{+1}$ represents the first nucleotide transcribed, Y=C, T; N=A, C, G, T; W=A, T (TCACATC in SEQ ID No: 2, variant 2). Downstream of the initiator site, extended and alternate blocks of poly(CAA) and poly(CT) follow, repeated for example twice. As we said, moreover, in order to promote the recognition of the ATG start codon, a Kozak or Kozak-like sequence may be present at the 3' terminal (for example in both variants it may be included in TCTAGA, corresponding to the restriction site for Xba I).

Compared with the type of leader described in WO 2008/080954, the artificial DNA sequence described here may therefore provide new specifications for making artificial 5'-UTRs. Such specifications, not provided in WO 2008/080954, can reflect into precise compositional and structural modifications of the leader region and into new preferential applications.

The entity of variations can be inferred, by way of example, by comparing the LLTCK sequence described in WO 2008/080954 with the example variants of STE leader described above. The latter do not have any sequences definable as A/T-rich elements (AU-rich elements, AREs), nor ATT triplets which instead are present in LLTCK downstream of the Inr site, internally and at the sides of the octamer of the TMV Ω leader.

To demonstrate the greater efficiency of the new STE leader, a comparison was made between it and the LLTCK sequence described in WO 2008/080954, analyzing the expression levels of two reporter genes in unrelated plant species, such as tobacco (Nicotiana tabacum L.) and rice (Oryza sativa L.).

In tobacco, the gene considered was uidA (GUS) and the constructs used for genetic transformation, that is, 35S-LLTCK::uidA::NOS ter (pSTART) and 35S-STE::uidA::NOS ter (pSTART-STE), were obtained by replacing the leader sequence present in pBI121 (Clontech) by LLTCK and STE, respectively (Example 1). More precisely, it was the sequence pBI121 that was replaced and manipulated, comprised between the Inr 35S region of CaMV (ACACG), kept common to both constructs, and the restriction site Xba I (TCTAGA). The expression levels of the reporter gene were assessed using a fluorometric 4-MUG assay (Jefferson et al., 1987), characterized by considerable sensitivity, precision, speed and ease of execution. In particular, to quantitatively assess the expression of the GUS gene in transformed plants, fluorometric assays were carried out on crude protein extracts derived from pressing three, completely distended, young leaves. The values of specific activity for β-glucuronidase (GUS), expressed in millimoles of 4-MU produced per mg of protein, were normalized in relation to the total protein concentration calculated using a Bradford assay. FIG. 1 shows the data obtained on the transformed plants with the two constructs (average of the values recorded for the three leaf extracts) in decreasing order.

A statistical analysis was carried out on the data shown in FIG. 1, in this case a one-way analysis of the variance (ANOVA), the results of which are shown in the following Table 1.

TABLE 1

ANOVA carried out on the mean data obtained in plants transformed with the constructs 35S-LLTCK:::uidA::NOS ter and 35S-STE::uidA::NOS ter.

| SUMMARY | | | | |
|---|---|---|---|---|
| Groups | Count | Sum | Mean | Variance |
| pSTART | 20 | 3.985 | 0.199 | 0.151 |
| STE | 23 | 12.973 | 0.564 | 0.514 |

| ANALYSIS OF VARIANCE | | | | | |
|---|---|---|---|---|---|
| Origin of variance | SQ | gdl | MQ | F | Value of significance |
| Between groups | 1.424 | 1 | 1.424 | 4.119* | P < 0.05 |
| Within groups | 14.169 | 41 | 0.346 | | |
| Total | 15.593 | 42 | | | |

The analysis showed the existence of statistically significant differences (P<0.05) between the two populations analyzed (pSTART and pSTART-STE). From the joint examination of Table 1 and FIG. 1 it is possible to assert that the STE leader causes non-marginal increases in the expression levels of uidA. In particular, if the mean values obtained are considered in the two populations of transformed plants, the STE leader leads to an increase in the expression levels of the reporter gene GUS about 2.8 times compared to LLTCK.

In confirmation of what was seen in tobacco (model species for the class of dicots), experiments were also carried out on rice, a cereal widely used in the biotechnological field. As with the first species, the comparison was carried out with two expression constructs, exactly like other elements. In particular, the following vectors were compared:

pCAMBIA1300/PMI/GluB4-LLTCK::GCasi::GluB4ter;
pCAMBIA1300/PMI/GluB4-STE::GCasi::GluB4ter.

However, we must underline that in rice the effect of a different type of leader was assayed in a context of seed-specific expression, using different control elements. More precisely, the promoter of glutelin 4 of rice (GluB4) was used, and the corresponding terminator (GluB4ter). As reporter gene, hGCasi was chosen, that is, the sequence encoding the human enzyme acid beta-glucosidase; the detection of the recombinant protein can be carried out with considerable sensitivity and precision through an immunological assay (DAS-ELISA). With regard to the leader sequence, in both vectors the Inr site of GluB4 was used, since it comes within the eukaryotic consensus sequence YYANWYY. Moreover, the transcription start site of the CaMV 35S promoter appeared less suitable because this virus attacks only dicot plants.

Figure 2:
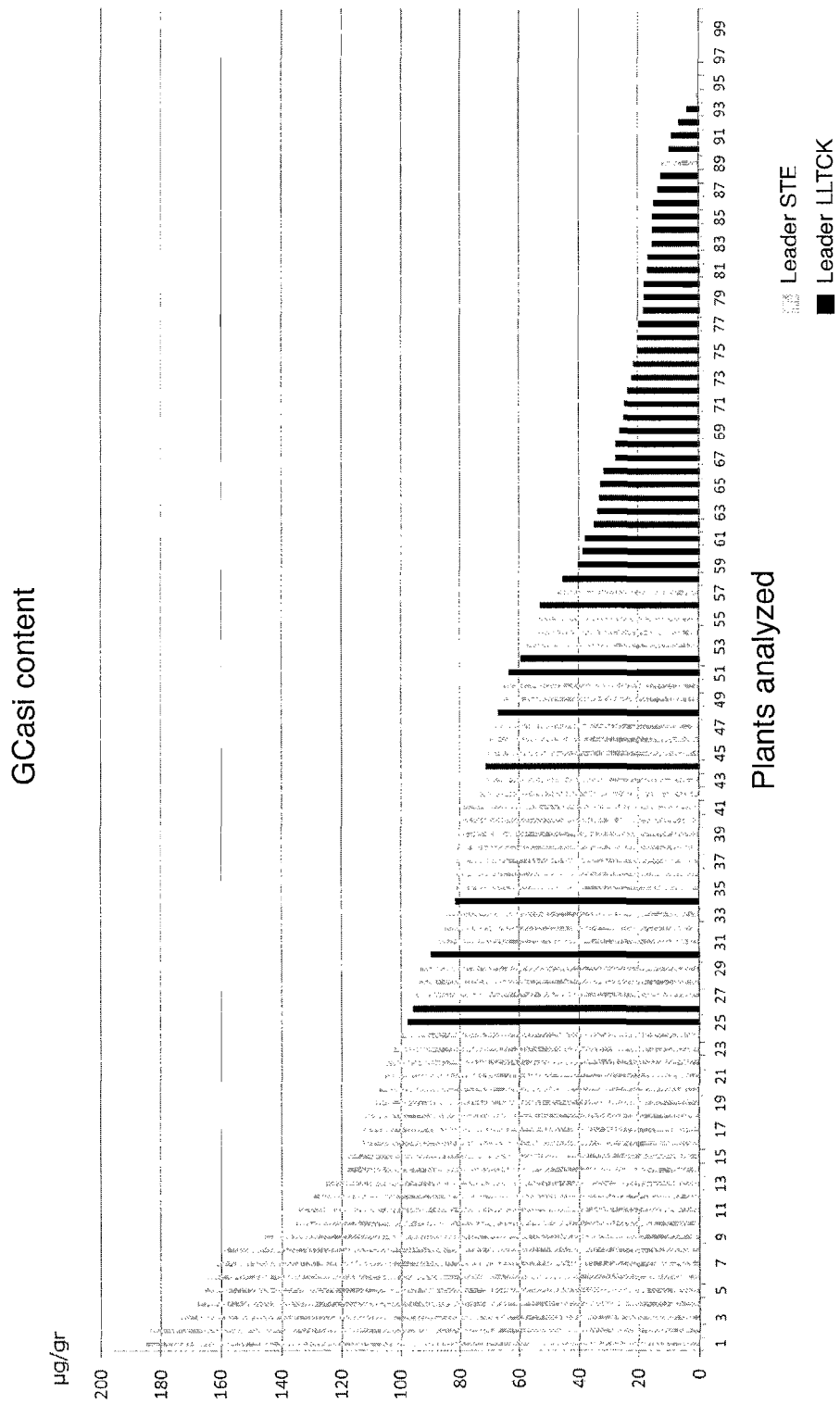
FIG. 2 shows the distribution of the GCasi protein content, assessed using a DAS-ELISA assay and expressed in μg GCasi per gram of rice flour, in plants bearing the LLTCK leader and the STE leader.

Each vector was inserted into *Agrobacterium tumefaciens* using electroporation for the transformation of *Oryza sativa*, var. CR W3 (Hiei et al., 1994). Two populations of transgenic plants were obtained, each consisting of 50 individual plants. The mature seeds of each plant were collected and used for total proteins extraction. The protein extracts obtained were analyzed in DAS-ELISA to assess the GCasi content. FIG. 2 shows the distribution of the data obtained.

The one-way analysis of variance allowed to establish that the differences in expression of the reporter gene found between the two populations of rice considered are statistically significant (Table 2).

TABLE 2

ANOVA performed on the data obtained in transformed plants with the constructs pCAMBIA1300/PMI/GluB4-LLTCK::GCasi::GluB4ter and pCAMBIA1300/PMI/GluB4-STE::GCasi::GluB4ter.

SUMMARY

| Groups | Count | Sum | Mean | Variance |
| --- | --- | --- | --- | --- |
| STE Leader | 50 | 5052.015 | 101.040 | 1714.609 |
| LLTCK Leader | 50 | 1468.772 | 29.375 | 643.617 |

ANALYSIS OF VARIANCE

| Origin of variance | SQ | gdl | MQ | F | Value of significance |
| --- | --- | --- | --- | --- | --- |
| Between groups | 128396.3296 | 1 | 128396.330 | 108.892* | $P < 0.05$ |
| Within groups | 115553.0807 | 98 | 1179.113 | | |
| Total | 243949.4102 | 99 | | | |

From Table 2 and the graph in FIG. 2 shown above it is clear that the STE leader gives expression levels certainly greater than the LLTCK leader. In particular the STE leader causes an increase in the expression levels of the reporter GCasi gene about 3.5 times those of LLTCK.

EXAMPLES

Example 1

Production of the Expression Vector in Tobacco pSTART-STE

Figure 3A:
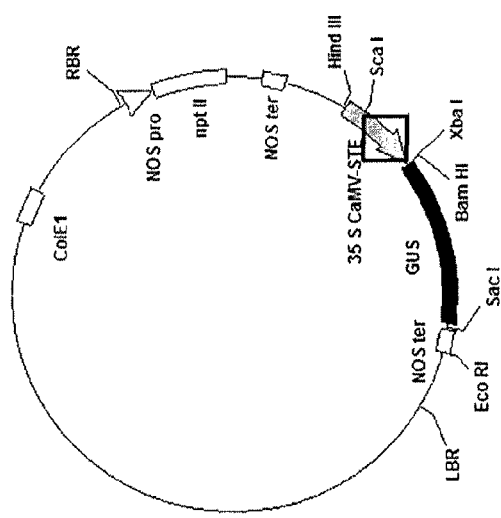
FIG. 3A shows the diagram of the expression vector in tobacco pSTART-STE, where:
RBR: right border repeat
LBR: left border repeat
35S CaMV: promoter 35S of the cauliflower mosaic virus
GUS: reporter protein
NOS ter: terminator of the Nopaline synthase of *Agrobacterium tumefaciens*
Figure 3B:
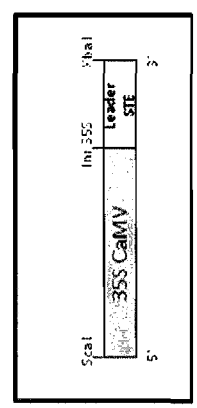
FIG. 3B shows the artificially synthesized tract containing a part of the CaMV 35S promoter (from the site Sca I) and the STE leader.

The starting point for the production of the vector pSTART-STE was the expression vector pSTART, obtained in a previous work (De Amicis et al., 2007). This last vector, in turn obtained from a modification of the original vector pBI121 (Clontech), has an expression cassette consisting of the CaMV 35S promoter with LLTCK leader, the reporter gene encoding the GUS protein and the NOS terminator. To obtain pSTART-STE (FIG. 3A), the LLTCK leader in pSTART was replaced by the STE leader. To this purpose the sequence corresponding to a part of the 35S promoter (from the Sca I site) was artificially synthesized, to which the sequence of the STE leader was added, in this case in the example form SEQ ID No: 1. The synthesized tract (702 bp, FIG. 3B) was replaced in pSTART by digestion with restriction enzymes Sca I and Xba I, recovery of the vector and ligation with DNA ligase of the new synthesized sequence.

Example 2

Production of Expression Vectors with Promoter GluB4 and Leaders LLTCK and STE

Figure 4A:
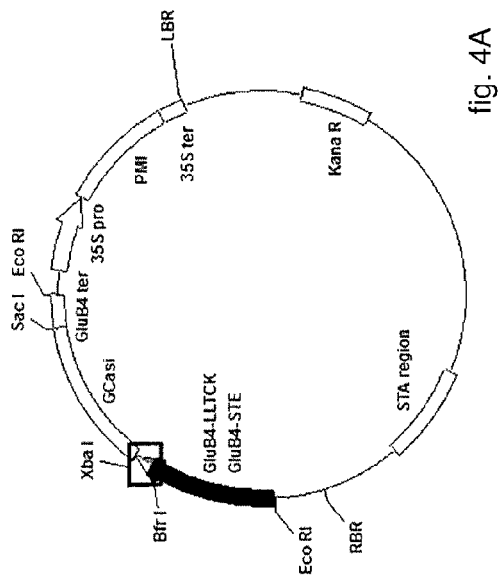
FIG. 4A shows the diagram of the expression vectors in rice pCAMBIA1300/PMI/GluB4-LLTCK/STE::GCasi::GluB4 ter; where:
RBR: right border repeat
LBR: left border repeat
GluB4-LLTCK: glutelin 4 promoter of rice with LLTCK leader
GluB4-STE: glutelin 4 promoter of rice with STE leader
GCasi: gene coding for the human enzyme acid beta-glucosidase (hGCasi)
GluB4 ter: glutelin 4 terminator of rice
35S pro: CaMV 35S promoter
PMI: gene coding for phosphomannose isomerase (selection marker of the transformed plants)
35S ter: CaMV 35S terminator
Figure 4B:
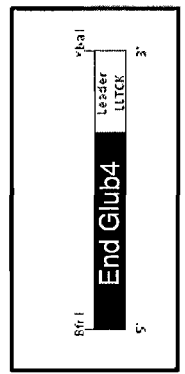
FIGS. 4B and 4C represent respectively the artificially synthesized tract containing the final part of the GluB4 promoter (from the Bfr I site) and the leaders LLTCK and STE.
Figure 4C:

The leader sequences LLTCK and STE were artificially synthesized. In particular, in both cases, the synthesized tract corresponded to the sequence comprised between the site Bfr I, present in the terminal part of the glutelin 4 promoter of rice (GluB4) and the site Xba I, present at the 3' terminal of the leaders themselves (FIGS. 4B and 4C). More precisely, this tract resulted equal to by for LLTCK (FIG. 1B) and 315 bp for STE (FIG. 4C).

In order to produce the final expression vectors, a series of intermediate sub-cloning steps were carried out in parallel for the two leaders, which allowed the final assembly of the expression cassettes. In the initial step, the leader natively present downstream of the GluB4 promoter was replaced by the synthetic leaders LLTCK and STE. The starting point was the vector pGEM-T/GluB4-NAT, containing the promoter of glutelin 4 in fusion with the native leader (GenBank acc. no AY427571). The terminal tract of the GluB4 promoter (from the site Bfr I) and the native leader were eliminated by digestion with the enzymes Bfr I and Xba I and replaced by the new, synthesized sequences. In this way, two intermediate vectors were produced, pGEM-T/GluB4-LLTCK and pGEM-T/GluB4-STE, subsequently verified by PCR analysis, enzymatic digestion and sequencing.

The final expression cassettes were assembled starting from vector pUC18/GluB4ter. This vector was subjected to two successive sub-cloning steps for insertion of the complex GluB4-LLTCK (or GluB4-STE) and the reporter gene, respectively. In particular, in the first sub-cloning, pUC18/GluB4ter was digested with the restriction enzymes Sph I and Xba I in order to ligate the tracts GluB4-LLTCK and GluB4-STE, extracted from the vectors pGEM-T/GluB4-LLTCK and pGEM-T/GluB4-STE, respectively. In the second sub-cloning, the intermediate vectors pUC18/GluB4-LLTCK::GluB4ter and pUC18/GluB4-STE::GLUB4ter were opened by digestion with Xba I and Sac I in order to insert the reporter gene (hGCasi), in its turn extracted from the vector pMS/hGCasi using the same enzymes. In this way the two vectors pUC18 were obtained, containing the expression cassettes entirely assembled, that is, pUC18/GluB4-LLTCK::GCasi::GluB4ter and pUC18/GluB4-STE::GCasi::GluB4 ter.

In order to produce the final vectors, the two expression cassettes GluB4-LLTCK::GCasi::GluB4ter and GluB4-STE::GCasi::GluB4ter were extracted individually, for example by a double digestion with Eco RI from the respective pUC18 and cloned in the final expression vector pCAMBIA1300/PMI so as to constitute (FIG. 4A):
pCAMBIA1300/PMI/GluB4-LLTCK::GCasi::GluB4ter and pCAMBIA1300/PMI/GluB4-STE::GCasi::GluB4ter.

Example 3

Genetic Transformation of *Nicotiana tabacum* Mediated by *Agrobacterium tumefaciens*

For the genetic transformation of tobacco (*Nicotiana tabacum*, cv. Xanthi) mediated by *A. tumefaciens*, the Horsch et al. (1985) protocol was used. We shall now briefly describe the main steps of the whole procedure.
Disinfection of the Seeds
For the preparation of tobacco seeds to be used in the transformation, a disinfection was first carried out according to the following protocol:
Put a small quantity of seed in a sterile 2 mL test tube. Add about 1 mL of 95% ethanol. Keep for 2 min and stir vigorously. Eliminate the ethanol, using a pipette. Add 1 mL of 2% hydrochloride. Leave to incubate for 20 min, stir, eliminate and add 1 mL sterile water; rinse the seeds in this way 5 times. Leave the water from the last rinse in the test tube. Remove a certain quantity of seed and water, using a rod from which the tip has been removed under sterile conditions, and put it on an MS10 substrate in a plate or baby jar.
Using a bacteriological loop or a Pasteur pipette bent to an L-shape, distribute the seeds delicately.
Put the plates to germinate in the light inside a climatic chamber at 28° C.
Transformation with *A. tumefaciens*
The transformation of leaf material of *N. tabacum* using *A. tumefaciens* was done in the following steps:
under a hood, fill 4-5×2 mL test tubes with 1.8 mL sterile LB-broth. Inoculate the *A. tumefaciens*, picking up with a sterile toothpick a small but visible quantity of bacterial colony grown on the plate, and dilute it in a test tube; stir vigorously;
take a tobacco leaf (from plants about 1-month old) and, using a sterile punch, make discs with a diameter of 7 mm from the leaf blade; using a pincer, put the leaf discs on a plate of MS10 substrate; put 30 discs per plate. For each bacterial strain obtain a total of at least 200 discs. Prepare two control plates on which to put discs that will not be infected and that will always stay on the MS10 medium;
infect the discs with *A. tumefaciens*; pour the content of a test tube, inoculated just before with the bacterium, onto the plate containing the discs. Stir gently with a rotational movement, so as to wet all the discs, then remove the excess liquid with a pipette. Arrange the discs regularly, using the pincers;
incubate the plates for one night in constant light at a temperature of 28° C. in a growth chamber;
transfer the leaf discs onto a substrate of MS10 Cefotaxime 500 mg/L;
incubate the plates for 6 days in constant light and at a temperature of 24° C.;
8 days after the start of the transformation, transfer the leaf discs onto a substrate of MS10 Cefotaxime 500 mg/L-Kanamycin 200 mg/L for the selection of the transformed calli. Incubate for 14 days under the same conditions;
cut the shoots consisting of at least two leaves, not chimeric and with a normal appearance. Transfer them onto a substrate for rooting (MS 0 with Cefotaxime 500 mg/L—Kanamycin 200 mg/L—IBA 2 mg/L);
transfer the rooted plants to potted peat or hydroponic culture system for growth, delicately cleaning the substrate from the roots with water. Arrange the plants in a climatic chamber maintaining a temperature of 26-30° C. with a light period of 16 hours light and 8 hours of darkness.

Example 4

Genetic Transformation of *Oryza sativa* Mediated by *Agrobacterium tumefaciens*

For the transformation of rice, variety CR W3, the Hiei et al. (1994) protocol was used, as modified by Hoge (Rice Research Group, Institute of Plant Science, Leiden University) and Guiderdoni (Biotrop program, Cirad, Montpellier, France) until the transformed calli were obtained. For the subsequent selection step the Datta and Datta (2006) protocol was applied. We shall now briefly describe the main steps of the whole procedure.
Preparation and Development of Embryogenic Calli from Rice Scutellum
The transformation of rice was done using embryogenic calli deriving from the scutellum.
In order to induce proliferation of calli from scutellum tissue, the following operating protocol was used:
the rice seeds were husked (elimination of the glumes);
to eliminate potential contaminant pathogens and saprophytes able to interfere with the production of the calli, the caryopses, without the glumes, were disinfected;
a. in the first disinfection treatment, the husked seeds remained for 2 min in a 70% ethanol solution;
b. after the ethanol treatment, the seeds were transferred to a solution of 5% sodium hydrochloride with 2 drops of Tween20 detergent and kept there in slow stirring for 30 min;
c. to eliminate all traces of sodium hydrochloride which might inhibit the induction of calli in the scutella, a series of washes were carried out, in sterile water, each lasting 15 min;
after the last wash, the seeds were dried on sterile absorbent paper;
12 seeds per plate were positioned on the surface of the substrate used to induce calli (CIM, callus-induction medium), dispensed in a volume of 25 mL inside the Petri dishes (Ø90 mm);

the plates thus obtained were incubated in the dark, at a temperature of 28° C. for 21 days; after 1 week of incubation, the endosperm and the rootlets were eliminated to promote the development of the callus from the scutellum (the scutellum is recognized by its compact mass, partly included in the endosperm, yellow in color);

after 3 weeks of induction, the callus was transferred onto fresh CIM substrate, and then the callus masses were broken up, without using scalpels, following the fracture lines naturally present on the callus;

the sub-culture was continued for another 10 days so as to develop the embryogenic callus and make it suitable for transformation.

Co-Cultivation of the Calli with *A. tumefaciens* EHA 105

1. To obtain sufficient quantities of *A. tumefaciens* for the transformation, the strains bearing the above-mentioned plasmid vectors (Example 2) were incubated for 3 days at 30° C. in LB-agar;
2. when *agrobacterium* was grown, the bacterial cell layers were scraped off and suspended in the co-cultivation medium liquid (CCML), until an $O.D._{600}$ of about 1.0 was obtained, corresponding to $3\text{-}5\cdot10^9$ cells/mL;
3. the best calli, that is, those with a diameter of about 2 mm, compact and with a whitish color, were transferred to a Petri dish containing 35 mL of bacterial suspension and left in immersion for 15 min, stirred;
4. then the callus was dried, using sterile absorbent paper;
5. a maximum number of 20 calli was transferred per high-edge Petri dish (Sarstedt) containing the semisolid substrate for co-cultivation (CCMS, co-cultivation medium solidified);
6. the calli were then incubated in a dark environment, at a temperature of 25° C. for 3 days.

Selection of the Calli Based on the PMI Marker System

After the co-cultivation of the embryogenic rice calli with the *agrobacterium*, the transformed tissues were selected, using the selection system based on PMI (phosphomannose isomerase) as selectable marker and mannose as the selective agent. This method provides to use cultivation substrates containing increasing concentrations of mannose and decreasing concentrations of sucrose.

The procedure used was as follows:

transfer of the calli from co-cultivation with *A. tumefaciens* onto a PSM (pre-selection medium) substrate with no mannose and containing 3% sucrose; incubation for 1 week in the dark at a temperature of 28° C.;

transfer of the calli onto a SMI (selection medium I) substrate containing 2% sucrose and 1.5% mannose and incubation for 2 weeks in the dark at a temperature of 28° C.;

transfer of the calli onto a SMII (selection medium II) substrate containing 1% sucrose and 2% mannose and incubation for 2 weeks in the dark at a temperature of 28° C.;

regeneration follows.

Regeneration of Rice Plants from Transformed Calli

The regeneration of the plants putatively transformed occurred thanks to a suitable hormonal stimulation of the transformed callus following the procedure reported here:

1. the selected embryogenic rice calli were transferred onto high-edge Petri dishes containing the PRM substrate (pre-regeneration medium) containing 0.5% sucrose and 2.5% mannose and incubation in the dark for 2 weeks at a temperature of 28° C.;
2. after the passage on the PRM substrate the calli were transferred onto the RM substrate (regeneration medium), without mannose, to a maximum number of 8-10 units per high-edge Petri dish. The plants were grown in light, at 28° C. for 3-4 weeks.
3. when the plants were grown enough to be separated from the callus (>3 cm high), they were transferred to cultivation tubes containing 25 mL of the rooting medium (rm);
4. the sub-culture inside the tubes continued for about 3 weeks always at about 28° C., in light;
5. at the end of the regeneration process, the plants were transferred to peat and grown under glasshouse conditions.

Example 5

Extraction of Total Proteins from Leaf Tissue of Tobacco Transformed by 4-MUG Assay The procedure now described allows to produce and preserve leaf extracts of tobacco, retaining the enzyme activity of the GUS protein for a long time.

In a 1.5 mL test tube, weigh 15 mg PVP (polyvinylpyrrolidone, MW>40000 g/mol) and add 200 µL of extraction buffer (see Table 3), vortex stir and leave in incubation at 4° C. for at least 30 min;

Extract leaf juice using a Meku Pollähne press;

Remove 100 µL of juice and add it to the buffer-PVP mixture, keeping all of it in ice;

Centrifuge for 15 min at 4° C. at 11500×g;

Remove the supernatant (~200 µL) and transfer it very quickly to a new test tube;

Freeze immediately using liquid nitrogen and preserve at −80° C.

TABLE 3

Composition of the extraction buffer

| Components | Quantities per 100 mL |
|---|---|
| $NaHPO_4$ pH 7.0 | 5 mL from stock 1M |
| DTT 5 mM | 0.5 mL from stock 1M |
| 1 mM $Na_2EDTA$ | 0.2 mL from stock 0.5M |
| Sodium Lauryl Sarcosine 0.1% | 1 mL from stock 10% |
| Triton X-100 0.1% | 1 mL from stock 10% |
| In volume with $H_2O$ | 100 mL |

The procedure was applied without distinction to all the samples subjected to fluorometric analysis. Each transformed plant was analyzed in triplicate using extracts taken from 3 leaves (advanced expansion stage) present in the apical part of the plant.

Example 6

Fluorometric 4-MUG Assay

To assess the content of the GUS enzyme in the protein leaf extracts obtained from the transformed plants, a specific fluorometric assay was made. The substrate used was 4-Mehylumbelliferyl-β-D-glucuronide (MUG), which generates the fluorescent compound 4-methylumbelliferone (4-MU) in presence of the GUS enzyme. The following protocol was derived from the standard procedure indicated by Jefferson (1987), and was adapted to perform the assay in plates.

In a 96-well plate (low binding, Sarstedt) add 10 µL of leaf extract to 130 of MUG solution (Table 4);
Leave in incubation for 1 h at 37° C.;
Remove 20 µL of reaction and add it quickly to 230 µL of Na$_2$CO$_3$ 0.2 M (stop solution) in an opaque plate with 96 wells (repeat at least twice per sample);
In the opaque plate perform a calibration curve with 4-MU (1 mM and successive dilutions 1:2 for a total of 4-5 points);
Read the values using a plate fluorometer;
Process the results using a Curve Fitting Data Analysis (Promega) software.

TABLE 4

Composition of the 4-MUG solution

| Components | Quantities per 100 mL |
|---|---|
| MUG (MW 352.3) 1.2 mM | 0.042 g |
| Extraction buffer GUS (Table 3) | 100 mL |

Example 7

Extraction of Total Proteins from Transformed Rice Seeds

To obtain extracts of total proteins to be assayed using DAS-ELISA, an extraction protocol was developed which included the following steps.
Ripe ears were taken from each individual;
The ears were dried in a dry and aired place for about 3 days until a relative humidity of the seed of 14% was obtained;
Random sampling of 40 seeds for each line;
The seeds were husked with a manual rice husker;
The sample was ground with an MM2 (Retsch) vibration micro-mill at a speed of 20 Hz for 2 minutes and 70 mg of the flour obtained were removed;
The flour was homogenized in a mortar with 1 mL of extraction buffer (Tris-HCl 50 mM, NaCl 0.5 M, pH=7.0);
Subsequent dilution with another 7 mL of the same buffer;
Incubation whilst continuously stirred at 4° C. for 1 h;
1 mL removed and centrifuged at 20000×g for 40 min at 4° C.;
The liquid phase containing the proteins was recovered, and preserved at −20° C.

Example 8

DAS-ELISA Analysis

The DAS-ELISA assay, based on a double immunological recognition, was used to assess the GCasi content of the individual protein extracts. For the analysis, the samples were diluted 1:30. We shall now report the main steps of the assay:
Distribute in each well 100 µL of the non-conjugated polyclonal antibody anti-GCasi diluted at 2 ng/µL in a coating solution (PBS diluted 1:5, sodium azide (0.01%);
Incubate the plate overnight at 4° C.;
Remove the antibody;
Distribute 250-300 µL blocking solution (PBS+BSA 2.5%+sodium azide 0.01%) in each well;
Incubate the plate at 25° C. for 20 min;
Remove the blocking solution;
Distribute 50 µL/well of each dilution of the standard (200, 100, 50 and 25 pg/µL commercial imiglucerase; Sanofi-Genzyme), of each sample to be analyzed and of the control sample, consisting of the dilution solution (PBS+Tween20 0.1%+BSA 1%);
Incubate the plate for 30 min at 37° C. while stirring;
Wash the wells 3 times with 300 µL/well of washing solution (PBS+Tween20 0.1%);
Distribute 50 µL/well of polyclonal antibody anti-GCasi conjugated with horseradish peroxidase, diluted at 0.4 ng/µL dilution solution;
Incubate the plate for 30 min at 37° C. while stirring;
Wash the wells 3 times with 300 µL/well of washing solution (PBS+Tween20 0.1%);
Distribute 100 µL/well of TMB solution;
Incubate the plate for about 10 min at 25° C.;
Stop the reaction with stop solution (hydrochloric acid 1M) 100 µL/well;
Read the plate at 450 nm with plate reader Modulus II (Promega);
Process the data using Curve Fitting Data Analysis software (Promega), assigning the known concentration values of the standards. The concentration values of the samples were obtained using a linear curve with four parameters, considering the dilution factor adopted in order to obtain the real concentrations of the extracts.

BIBLIOGRAPHY

Beerman R W, Jongens T A (2011) A non-canonical start codon in the *Drosophila* fragile X gene yields two functional isoforms. Neuroscience 181: 48-66

Bradford M. M. (1976) Rapid and sensitive method for the quantitation of microgram quantities of protein utilizing the principle of protein-dye binding. Anal. Biochem. 72: 248-254

Franks TM, Lykke-Andersen J (2008) The control of mRNA decapping and P-body formation. Mol Cell. 32(5): 605-615

Gallie D R, Walbot V (1992) Identification of the motifs within the tobacco mosaic virus 5'-leader responsible for enhancing translation. Nucleic Acids Res 20: 4631-4638

Gerashchenko M V et al. (2010). CUG start codon generates thioredoxin/glutathione reductase isoforms in mouse testes. The Journal of Biological Chemistry, 285: 4595-4602

Guilley H et al. (1982) Transcription of Cauliflower Mosaic Virus DNA: detection of promoter sequences, and characterization of transcripts. Cell 30: 763-773

Jefferson R A, 1987. Assaying chimeric genes in plants: the GUS fusion gene system. Plant Molecular Biology Reporter 4: 387-405

Schmitz J et al. (1996) Non canonical translation mechanisms in plants: efficient in vitro and in planta initiation at AUU codons of the tobacco mosaic virus enhancer sequence. Nucleic Acids Res 24: 257-263

Simpson G G et al. (2010) Non-canonical translation initiation of the *Arabidopsis* flowering time and alternative polyadenylation regulator FCA. The Plant Cell 22: 3764-3777

Tyc K et al. (1984) Multiple ribosome binding to the 5'-terminal leader sequence of tobacco mosaic virus RNA. Assembly of an 80S ribosome X mRNA complex at the AUU codon. Eur J Biochem. 140(3): 503-511

The invention claimed is:

1. An artificial DNA of a 5'-UTR leader region wherein the artificial DNA is operably linked to a sequence encoding a recombinant protein in a plant, and wherein expression in a plant of the sequence encoding the recombinant protein is more than about 2.8 times higher when compared with expression when operably linked to SEQ ID NO: 3,
   said artificial DNA comprising, along the 5' to 3' direction, an Inr initiator site and a Kozak or Kozak-like consensus sequence, wherein the Kozak or Kozak-like consensus sequence is a sequence that requires the presence of a purine in the third position upstream of the translation start codon,
   said artificial DNA further comprising, between the Inr initiator site and the Kozak or Kozak-like consensus sequence, two poly(CAA) or $(CAA)_n$ regions, each formed by an oligonucleotide that consists of two or more copies of a CAA element contiguous with each other, two poly(CT) or $(CT)_m$ regions in the same number as the poly(CAA) regions and each formed by an oligonucleotide that consists of two or more copies of a CT element contiguous with each other,
   wherein one poly(CAA) region, in the 5' to 3' direction, is upstream of a poly(CT) region and one poly(CAA) region, in the 5' to 3' direction, is contiguous with a poly(CT) region,
   with the provisions that said artificial DNA does not contain any of the following components: A/T-rich motifs, trinucleotide elements ATT, trinucleotide elements CTG and homopolymeric tracts, that is, sequences consisting of more than 3 identical nucleotides, wherein the A/T-rich motifs are defined as tracts or sequences consisting of more than 3 nucleotides adenine (A) and/or thymine (T), in any combination thereof.

2. The artificial DNA according to claim 1, wherein m is an integer, which can be selected equal or different among the poly(CT) regions, greater than or equal to 2, optionally comprised between 3 and 5.

3. The artificial DNA according to claim 1, containing two poly(CAA) regions and two poly(CT) regions, wherein a first poly(CAA) region is upstream of a first poly(CT) region and a second poly(CAA) region is downstream of said first poly(CT) region and upstream of a second poly(CT) region.

4. The artificial DNA according to claim 1, wherein the Inr initiator site is the transcription start site
   5'-ACACG-3' of CaMV 35S or is an Inr initiator site with consensus sequence
   5'-YYANWYY-3', wherein:
   Y=C, T;
   N=A, C, G, T;
   W=A, T.

5. The artificial DNA according to claim 1, comprising the sequence shown in SEQ ID NO: 1.

6. The artificial DNA according to claim 1, comprising the sequence shown in SEQ ID NO: 2.

7. The artificial DNA according to claim 1, wherein the A/T-rich motifs are defined as tracts or sequences consisting of more than 4 nucleotides adenine (A) and/or thymine (T), in any combination thereof.

8. The artificial DNA according to claim 1, wherein said artificial DNA does not contain the octamer ACAATTAC.

9. An expression vector comprising the artificial DNA according to claim 1.

10. A method for the production of recombinant proteins in plants, comprising the transformation of the plants using an expression vector according to claim 9.

11. The artificial DNA according to claim 1, wherein n is an integer, which can be selected equal or different among the poly(CAA) regions, between 3 and 9.

12. The artificial DNA according to claim 1, wherein n is an integer, which can be selected equal or different among the poly(CAA) regions, between 4 and 8.

13. The artificial DNA according to claim 1, wherein n is an integer, which can be selected equal or different among the poly(CAA) regions, between 5 and 7.

14. The artificial DNA according to claim 1, wherein the artificial DNA has a GC content of less than 50%.

* * * * *